United States Patent [19]

Seitz et al.

[11] Patent Number: 4,723,039
[45] Date of Patent: Feb. 2, 1988

[54] PHENYLACETALDEHYDES SUBSTITUTED BY BASIC GROUPS, THEIR PREPARATION AND DRUGS CONTAINING THESE COMPOUNDS

[75] Inventors: Werner Seitz, Plankstadt; Verena Baldinger, Heidelberg; Josef Gries, Wachenheim; Dieter Lenke, Ludwigshafen; Manfred Raschack, Weisenheim am Sand; Klaus Ruebsamen, Neustadt, all of Fed. Rep. of Germany

[73] Assignee: BASF Aktiengesellschaft, Ludwigshafen, Fed. Rep. of Germany

[21] Appl. No.: 937,716

[22] Filed: Dec. 4, 1986

[30] Foreign Application Priority Data

Dec. 5, 1985 [DE] Fed. Rep. of Germany ....... 3542994

[51] Int. Cl.$^4$ .............................................. C07C 95/08
[52] U.S. Cl. ..................... 564/344; 128/668; 128/672; 514/926; 564/342; 564/345; 568/424
[58] Field of Search ............... 568/424, 433; 564/344, 564/342, 345

[56] References Cited

U.S. PATENT DOCUMENTS

| | | | |
|---|---|---|---|
| 2,628,255 | 2/1953 | Sexton | 568/427 |
| 3,261,859 | 7/1966 | Dengl | 564/342 |
| 3,927,110 | 12/1975 | Watson | 568/427 |
| 4,438,131 | 3/1984 | Ehrmann et al. | 568/424 |

FOREIGN PATENT DOCUMENTS

| | | | |
|---|---|---|---|
| 64158 | 3/1985 | European Pat. Off. | 568/342 |
| 747866 | 4/1952 | United Kingdom | 568/424 |

OTHER PUBLICATIONS

Arzneim-Forsch/Drug Res., 31 (I), No. 5 (1981), pp. 773-780.
Drugs of Today, vol. 20, No. 2 (1984), pp. 69-90.

*Primary Examiner*—Werren B. Lone
*Attorney, Agent, or Firm*—Keil & Weinkauf

[57] ABSTRACT

Phenylacetaldehydes which are substituted by basic groups, of the formula

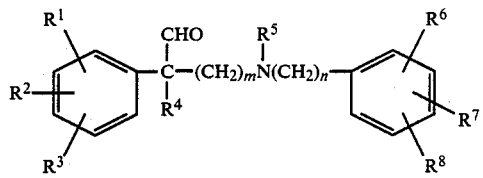

where $R^1$ to $R^8$, m and n have the meanings stated in the description, and their preparation are described. The substances are useful for the treatment of disorders.

9 Claims, No Drawings

PHENYLACETALDEHYDES SUBSTITUTED BY BASIC GROUPS, THEIR PREPARATION AND DRUGS CONTAINING THESE COMPOUNDS

The present invention relates to novel phenylacetaldehydes substituted by basic groups, their preparation and drugs which contain these substances.

German Patent No. 1,154,810 and European Laid-Open Application No. 64,158 describe phenylacetonitriles which are substituted by basic groups. From this class of compounds, verapamil and gallopamil have proven useful in the therapy of coronary heart diseases and of high blood pressure. Relationships between the chemical structure and biological action of the verapamil molecule have been described in various publications (cf. Arzneim. Forsch./Drug Res. 5 (1981), 773). On the basis of these structure/action considerations and experimental work, Mannhold [Drugs of Today 20 (2) (1984), 69–90] has shown that the nitrile group of the verapamil molecule is essential for the biological action.

We have found compounds which are highly effective in spite of the fact that the nitrile group has been converted.

The present invention relates to novel phenylacetaldehydes which are substituted by basic groups and are of the formula I

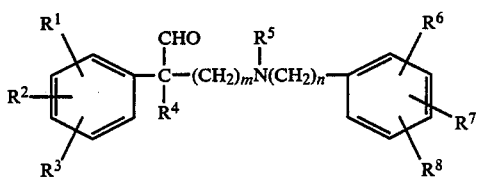

where $R^1$, $R^2$, $R^3$, $R^6$, $R^7$ and $R^8$ are identical or different and are each hydrogen, halogen, trifluoromethyl, $C_1$–$C_4$-alkyl, nitro or $C_1$–$C_4$-alkoxy, and two radicals in adjacent positions may furthermore together form methylene dioxy, ethylenedioxy, 1,3-dioxatetramethylene, propylene or butylene, $R_4$ is a saturated or unsaturated $C_1$–$C_{12}$-alkyl group, a cycloalkyl group or an aryl group, $R^5$ is $C_1$–$C_4$-alkyl and m and n are identical or different and are each 2, 3 or 4, and their salts with physiologically tolerated acids.

Preferred halogen atoms $R^1$ to $R^3$ and $R^6$ to $R^8$ are fluorine and chlorine. Preferred alkyl and alkoxy groups $R^1$ to $R^3$ and $R^5$ to $R^8$ are those of 1 or 2 carbon atoms. Preferred nitro compounds are those which contain one nitro group.

The following compounds are of particular interest:
(RS)-2-[3-[(phenylethyl)-methylamino]-propyl]-2-isopropylphenylacetaldehyde,
(R)-2-[3-[(phenylethyl)-methylamino]-propyl]-2-isopropylphenylacetaldehyde,
(S)-2-[3-[(phenylethyl)-methylamino]-propyl]-2-isopropylphenylacetaldehyde,
(RS)-2-[3-[(3-methoxyphenylethyl)-methylamino]-propyl]-2-isopropyl-3,4-dimethoxyphenylacetaldehyde,
(R)-2-[3-[(3-methoxyphenylethyl)-methylamino]-propyl]-2-isopropyl-3,4-dimethoxyphenylacetaldehyde,
(S)-2-[3-[(3-methoxyphenylethyl)-methylamino]-propyl]-2-isopropyl-3,4-dimethoxyphenylacetaldehyde,
(RS)-2-[3-[(3-methoxyphenylethyl)-methylamino]-propyl]-2-isopropyl-3,4,5-trimethoxyphenylacetaldehyde,
(R)-2-[3-[(3-methoxyphenylethyl)-methylamino]-propyl]-2-isopropyl-3,4,5-trimethoxyphenylacetaldehyde,
(S)-2-[3-[(3-methoxyphenylethyl)-methylamino]-propyl]-2-isopropyl-3,4,5-trimethoxyphenylacetaldehyde,
(RS)-2-[3-[(3,5-dimethoxyphenylethyl)-methylamino]-propyl]-2-isopropyl-3,5-dimethoxyphenylacetaldehyde,
(R)-2-[3-[(3,5-dimethoxyphenylethyl)-methylamino]-propyl]-2-isopropyl-3,5-dimethoxyphenylacetaldehyde,
(S)-2-[3-[(3,5-dimethoxyphenylethyl)-methylamino]-propyl]-2-isopropyl-3,5-dimethoxyphenylacetaldehyde,
(RS)-2-[3-[(3-ethoxyphenylethyl)-methylamino]-propyl]-2-isopropyl-3-ethoxyphenylacetaldehyde,
(R)-2-[3-[(3-ethoxyphenylethyl)-methylamino]-propyl]-2-isopropyl-3-ethoxyphenylacetaldehyde,
(S)-2-[3-[(3-ethoxyphenylethyl)-methylamino]-propyl]-2-isopropyl- 3-ethoxyphenylacetaldehyde,
(RS)-2-[3-[(3,5-diethoxyphenylethyl)-methylamino]-propyl]-2-isopropyl-3,5-diethoxyphenylacetaldehyde,
(R)-2-[3-[(3,5-diethoxyphenylethyl)-methylamino]-propyl]-2-isopropyl-3,5-diethoxyphenylacetaldehyde,
(S)-2-[3-[(3,5-diethoxyphenylethyl)-methylamino]-propyl]-2-isopropyl-3,5-diethoxyphenylacetaldehyde.

Examples of suitable physiologically tolerated acids are hydrochloric acid, hydrobromic acid, sulfuric acid, phosphoric acid, acetic acid, maleic acid, lactic acid, tartaric acid, citric acid and fumaric acid.

The novel compounds possess one or more asymmetric carbon atoms and are therefore obtained in the various enantiomeric forms. Consequently, the compounds I can be prepared either in optically active forms or as racemic mixtures. The racemates of the compounds I can be resolved into their optical antipodes by conventional techniques, for example by separation (fractional crystallization, column chromatography) of the diastereomeric salts. These salts can be prepared by reacting a compound I with a chiral acid. The enantiomeric forms can also be obtained by using optically active starting compounds.

The novel compounds are prepared by a process in which (a) a phenylacetonitile of the formula II

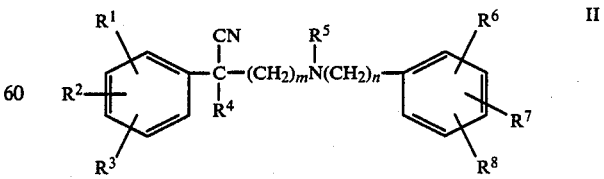

where $R^1$ to $R^8$, m and n are as defined above, is reacted with a complex aluminum hydride and the product is then hydrolyzed, or (b) a phenylacetaldehyde of the formula III

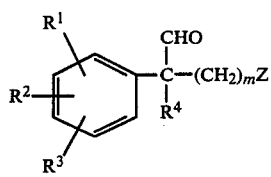

where $R^1$ to $R^4$ and m have the above meanings and Z is a leaving group, is reacted with a phenylalkylamine of the formula IV

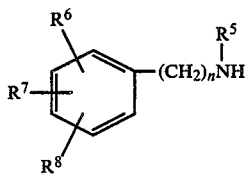

where $R^5$ to $R^8$ and n have the above meanings, and, if desired, the resulting compound is converted to a salt with a physiologically tolerated acid.

Complex aluminum hydrides which are suitable for reaction (a) include the following: lithium aluminum hydride, sodium bis-(2-methoxyethoxy)-aluminum dihydride, lithium and sodium triethoxyaluminum hydride and preferably diisobutylaluminum hydride.

The reaction is preferably carried out in an aprotic solvent, such as toluene or hexane, or in an aliphatic or cyclic ether, such as diethyl ether or tetrahydrofuran. The reaction temperature can be chosen to be from $-60°$ C. to $+20°$ C., but the reaction is preferably carried out at from $-20°$ to $0°$ C.

Reaction (b) is preferably carried out in a dipolar aprotic solvent, e.g. acetonitile, dimethylformamide or hexamethylphosphorotriamide, with the addition of an acid acceptor, e.g. anhydrous potassium carbonate. An additional equivalent of the phenylalkylamine of the formula IV may also be used as the acid acceptor. The reaction temperature can be chosen to be from room temperature to $120°$ C., but the reaction is preferably carried out at from $70°$ to $100°$ C.

Examples of suitable leaving groups are chlorine, bromine, iodine, sulfuric ester groups, mesylates and triflates.

Phenylacetaldehydes of the formula III can be obtained by reduction of the corresponding phenylacetonitriles with a complex aluminum hydride.

The compounds of the general formula I and their physiologically tolerated addition salts with acids have useful pharmacological properties. They are highly active Ca antagonists and have a dilatory effect on peripheral and central vessels, as well as protecting the heart and vessels from damage caused by increased Ca mobilization or Ca overloading. The compounds inhibit the secretion of gastric acid and have a cytoprotective and antiulcerous effect. Finally, they are capable of preventing or alleviating spasms of the bronchial muscles.

This is shown by the following experiments:

Inhibition of secretion of gastric acid

Inhibition of the secretion of gastric acid is evident from an increase in the pH of the surface of the gastric mucous membrane. For this measurement, groups of from 5 to 10 female Sprague-Dawley rats weighing 160–190 g, which had remained without food for 48 hours (water ad libitum), were pretreated with different doses of the test substances, administered orally. 1 hour later, a pH probe (Ingold 440 M₃) was inserted into the stomach under inhalation anesthesia with halothane, and the pH at the surface of the mucous membrane was measured (pH for untreated animals: $1.40 \pm 0.02$, $N = 200$). The dose which produces an increase in the pH by 0.75 pH units is determined as the ED 0.75, from the linear regression of log dose and the increase in the pH.

Cytoprotective action

The cytoprotective action was determined on groups of 8 female Sprague-Dawley rats weighing 160–190 g, the rats having received no food for 48 hours (water ad libitum) and having been pretreated with different doses of the test substances, administered orally. 1 hour later, 10 ml/kg of 100% ethanol were administered orally to the animals. After a further hour, the animals were sacrificed by inhalation of $CO_2$, the stomach was removed and the intensity of the lesions was assessed on the basis of the following scheme:

0 = unchanged mucous membrane
1 = a few areas of reddening which are narrow, elongated or small
2 = reddening over broad, elongated or large interrupted areas
3 = pronounced reddening which colors virtually the entire mucous membrane of the glandular stomach.

The dose which reduces lesions by 50% is determined as the ED 50% from the linear regression of log dose and the reduction in the intensity of the lesions of the gastric mucous membrane.

Antiulcerous action

To investigate the antiulcerous action, groups of 10 female Sprague-Dawley rats weighing 160–180 g received 1 mg/kg of reserpine, administered intraperitoneally, and thereafter remained without food for 18 hours (water ad libitum). After this time, the animals received 21.5 mg/kg of indomethacin, administered intraperitoneally, and the test substance administered orally. Thereafter, they were kept for 6 hours at $8°$ C. and then sacrificed. The stomach was removed and the area of the ulcerous lesions on the mucous membrane was determined. The dose which reduces the ulcerous area by 50% was determined as the ED 50%, from the linear regressions of the logarithms of the doses administered and the relative reduction in the area of ulceration, based on the control animals.

TABLE

Gastric acid secretion-inhibiting, cytoprotective and antiulcerous effects in the rat, oral administration

| Example No. | Acid secretion-inhibiting effect ED 0.75 (1) | Cytoprotective effect ED 50% | Antiulcerous effect ED 50% |
|---|---|---|---|
| Verapamil | 10.5 | (2) | (2) |
| 3 | 2.1 | 8.3 | 3.8 |
| 2 | 2.0 | 9.4 | 12.2 |

(1) Doses in mg/kg
(2) No effect

As demonstrated in Examples 3 and 2, the novel compounds inhibit secretion of gastric acid in doses which are one-fifth of than that required in the case of the comparative substance verapamil.

Moreover, they protect the gastric mucous membrane from the harmful effect of ethanol and prevent the formation of gastric ulcers.

The cytoprotective and antiulcerous actions are two additional effects, which are not shown by verapamil.

Hypotensive and antihypertensive action

To determine the hypotensive action, Sprague-Dawley rats weighing 230–280 g were anesthetized with urethane (1.78 g/kg, administered intraperitoneally). The blood pressure was measured in the carotid artery. The substances were administered intravenously into the jugular vein. The dose which produces a 20% decrease in blood pressure was calculated as the ED 20%, from the linear regression of log dose (mg/kg) and relative decrease in blood pressure (Δ%).

To determine the antihypertensive action, the substances were administered orally to spontaneously hypertensive male Okamoto rats (4–8 animals/dose, weight 270–360 g). The systolic blood pressure was measured noninvasively on the rat's tail with the aid of piezoelectric transducers, before and 2 hours after administration. The dose which reduces the systolic pressure by 20%, relative to the values for untreated control animals, was determined as the ED 20%.

TABLE

| | Hypotensive action | | | |
|---|---|---|---|---|
| | Reduction in blood pressure rat, anethetized, ED 20% i.v. | | Reduction in blood pressure SH rat ED 20% p.o. | |
| Example No. | mg/kg | R.A. | mg/kg | R.A. |
| Verapamil | 0.34 | 1.0 | 25 | 1.00 |
| 12 | 0.30 | 1.13 | 4.0 | 6.25 |

As shown in the table, when administered intravenously to the anesthetized rat, the substance of Example 12 reduces the blood pressure to a somewhat greater extent than verapamil.

It proves particularly effective when administered orally to conscious spontaneously hypertensive rats. In this model, the substance of Example 12 reduces the blood pressure when administered in a dose which is 6.3 times smaller compared with verapamil.

Broncholytic action

To test the broncholytic action, guinea pigs weighing from 300 to 450 g were anesthetized with urethane (1.5 g/kg, administered intraperitoneally) and, after preparation, with pentobarbital (25 mg/kg, administered intravenously), and cannulae were inserted into the trachea and the jugular vein.

The animals were artificially ventilated using a Starling pump. Bronchospasms were induced by injecting histamine (from 0.001 to 0.00464 mg/kg) or acetylcholine (from 0.02 to 0.04 mg/kg) 2–3 times at intervals of 10 minutes.

These bronchospasms were determined via inductive pressure transducers, using the method due to Konsett and Rössler (1940).

The substances, which were injected intravenously 5 minutes before the bronchospasms were induced, inhibited these bronchospasms in a dose-dependent manner.

For comparison, the dose which produces a 75% reduction in the bronchospasms was determined as the ED 75%, from the linear regressions of log dose and inhibition of spasms.

TABLE

Broncholytic action in the guinea pig, intravenous administration

| | ED 75%, mg/kg | |
|---|---|---|
| Example No. | Histamine-induced bronchospasm | Acetylcholine-induced bronchospasm |
| Verapamil | 1.3 | 0.56 |
| 8 | 0.38 | 0.23 |
| 6 | 0.59 | 0.39 |
| 7 | 0.61 | 0.67 |
| 12 | 0.65 | 0.27 |

The table shows the broncholytic activity of the novel substances and demonstrates that the substances of Examples 8, 6, 7 and 12 have a substantially higher activity compared with the reference substance verapamil.

Calcium-antagonistic action in spiral strips of aorta

The Ca-antagonistic action was tested on spiral strips of aorta of male and female Sprague-Dawley rats weighing from 200 to 300 g.

The animals were sacrificed with ether, and the thorax and thoracic aorta were removed. A maximum of 6 spiral strips about 2 mm wide and 2 cm long were used per animal.

The strips of aorta were suspended in a modified tyrode solution at 37° C. and subjected to an initial tension with a load of 1.5 g and, after a relaxation time of about 1 hour, Ca was removed by keeping them for 5 minutes in Ca-free tyrode solution with the addition of 0.2 mM of Na EDTA.

The Ca-free strips of vessel were depolarized with K-rich tyrode solution for 10 minutes. Contraction was induced by a $CaCl_2$ concentration of 0.5 mM. After 15 minutes, Ca was again removed from the strips of vessel by means of a Ca-free tyrode solution containing 0.2 mM of Na EDTA.

Depolarization was then effected again for 10 minutes with K-rich tyrode solution, after which 0.05 ml of the test substance was added. After the test substance had been allowed to act for 15 minutes, $CaCl_2$ was again added in a concentration of 0.5 mM in order to check whether the test substance has a Ca-antagonistic action. Inhibition of the effect of 0.5 mM $Ca^{++}$ by the antagonistic substance is stated as a percentage. The concentration which produces 50% inhibition of the Ca effect is determined as the EC 50% (on not less than 12 strips of vessel).

TABLE

Ca—antagonistic action in isolated spiral strips of aorta of the rat (administered in vitro)

| Example No. | EC 50%, mol/l |
|---|---|
| Verapamil | $3.5 \times 10^{-8}$ |
| 7 | $2.2 \times 10^{-8}$ |
| 12 | $3.2 \times 10^{-8}$ |
| 11 | $1.2 \times 10^{-8}$ |
| 10 | $1.9 \times 10^{-8}$ |
| 9 | $1.2 \times 10^{-9}$ |

The table shows the Ca-antagonistic of the novel substances and indicates that the substances of Examples 11, 10 and 9 have a substantially higher activity compared with the reference substance verapamil.

Because of these effects, they can be used, for example, for the prophylaxis and treatment of coronary heart disease, as antihypertensive agents for the treatment of high blood pressure, for peripheral and central disturbances of blood flow and for cerebral oxygen deficiency.

They can also be employed for gastric disorders accompanied by hypersecretion, for the treatment of gastric and duodenal ulcers and as broncholytics for bronchospastic conditions.

The novel compounds can be administered orally or parenterally in a conventional manner. The dose depends on the age, condition and weight of the patient and on the route of administration. As a rule, the daily dose of active compound is from about 0.1 to 10 mg/kg of body weight in the case of oral administration and from 0.01 to 1.0 mg/kg of body weight in the case of parenteral administration. Normally, the daily dose is from 1 to 5 mg/kg for oral administration and from 0.05 to 0.25 mg/kg for parenteral administration.

The novel active compounds can be brought into the conventional pharmaceutical forms, such as tablets, coated tablets, solutions, emulsions, powders, capsules or depot forms, and the conventional pharmaceutical auxiliaries and the conventional production methods may be employed for their preparation. Appropriate tablets can be obtained, for example, by mixing the active compounds with conventional auxiliaries, for example inert diluents, such as calcium carbonate, calcium phosphate or lactose, disintegrating agents, such as corn starch or alginic acid, binders, such as starch or gelatine, lubricants, such as magnesium stearate or talc, and/or agents for achieving a depot effect, such as carboxypolymethylene, carboxymethylcellulose, cellulose acetate phthalate or polyvinyl acetate.

The tablets may furthermore consist of a plurality of layers. Correspondingly, coated tablets can be prepared by coating cores, prepared similarly to the tablets, with agents conventionally used in tablet coatings, for example collidone or shellac, gum arabic, talc, titanium dioxide or sugar. To achieve a depot effect or to avoid incompatibility, the core may also consist of a plurality of layers. The tablet shell too may consist of a plurality of layers in order to achieve a depot effect, and the auxiliaries stated above in connection with tablets may be used.

Syrups of the novel active compounds or combinations of active compounds may additionally contain a sweetener, such as saccharin, cyclamate, glycerol or sugar, and a flavor improver, for example flavorings, such as vanillin or orange extract.

They may furthermore contain suspending agents or thickeners, such as sodium carboxymethylcellulose, wetting agents, for example condensates of fatty alcohols with ethylene oxide, or preservatives, such as p-hydroxybenzoates.

Injectable solutions are prepared in a conventional manner, for examples with the addition of preservatives, such as p-hydroxybenzoates, or stabilizers, such as Komplexones, and are introduced into injection bottles or ampoules.

Capsules containing the active compounds or combinations of active compounds can be prepared, for example, by mixing the active ingredients with inert carriers, such as lactose or sorbitol, and encapsulating the mixture in gelatine capsules.

Suitable suppositories can be prepared, for example, by mixing the envisaged active compounds as combinations of active compounds with conventional carriers, such as neutral fats or polyethylene glycol or its derivatives.

The novel compounds are also suitable for combining with other pharmacodynamically effective substances, such as diuretics or platelet aggregation inhibitors.

The Examples which follow illustrate the invention without restricting it.

EXAMPLE 1

2-[3-[(Phenylethyl)methylamino]-propyl]-2-isopropylphenylacetaldehyde 180 ml of a 1M solution of diisobutylaluminum hydride in hexane were added dropwise, at $-5°$ C., to a solution of 33.4 g (0.1 mole) of 2-[3-[(phenylethyl)-methylamino]-propyl]-isopropylphenylacetonitrile in 400 ml of diethyl ether. The mixture was stirred for 1.5 hours, after which 500 ml of 10% strength sulfuric acid were added. 30 g of tartaric acid were introduced, the mixture was rendered alkaline with concentrated potassium hydroxide solution, and the ether phase was separated off and washed several times with sodium chloride solution. After the ether phase had been dried over sodium sulfate, the ether was distilled off, the remaining oily residue was dissolved in 300 ml of ethyl acetate, and hydrochloric acid in isopropanol was added. The mixture was left to stand overnight, after which the precipitated hydrochloride was filtered off under suction.

Yield: 31.5 g (85%) of hydrochloride

Mp. 166°–168° C.

The following were obtained in a similar manner:

EXAMPLE 2

(S)-2-[3-[(Phenylethyl)-methylamino]-propyl]-2-isopropylphenylacetaldehyde hydrochloride, mp. 182°–184° C.

$[\alpha]_{589}^{20} = -7.2°$ (c=20.1 mg/ml, ethanol, d=10 cm)

Analysis: calculated: C 73.9, H 8.6, Cl 9.5, N 3.8.
found: C 73.8, H 8.6, Cl 9.5, N 3.8.

EXAMPLE 3

(R)-2-[3-[(Phenylethyl)-methylamino]-propyl]-2-isopropylphenylacetaldehyde hydrochloride, mp. 182°–184° C., $[\alpha]_{589}° = +7.7°$ (c=20.1 mg/ml, EtOH, d=10 cm)

Analyis: calculated: C 73.9, H 8.6, Cl 9.5, N 3.8.
found: C 73.9, H 8.5, Cl 9.5, N 3.8.

(The optically active starting materials for the synthesis of the substances 2 and 3 are described in German Laid-Open Application DOS No. 3,344,755.)

EXAMPLE 4

2-[3-[(Phenylethyl)-methylamino]-propyl]-diphenylacetaldehyde

Analysis: calculated: C 84.1, H 7.9, N 3.8. found: C 83.9, H 7.8, N 3.8.

EXAMPLE 5

2-[3-[(3-Methoxyphenylethyl)-methylamino]-propyl]-2-dodecyl-3-methoxyphenylacetaldehyde Analysis: calculated: C 78.0, H 10.2, N 2.7. found: C 78.0, H 9.8, N 2.8.

EXAMPLE 6

2-[3-[(3-Methoxyphenylethyl)-methylamino]-propyl]-2-isopropyl-3,4-dimethoxyphenylacetaldehyde Analysis calculated: C 73.0, H 8.7, N 3.3. found: C 73.1, H 8.8, N 3.4.

EXAMPLE 7

2-[3-[(3-Methoxyphenylethyl)-methylamino]-propyl]-2-isopropyl-3-methoxyphenylacetaldehyde Analysis: calculated: C 75.5, H 8.9, N 3.5. found: C 75.4, H 9.0, N 3.5.

EXAMPLE 8

2-[3-[(3,4-Dimethoxyphenylethyl)-methylamino]-propyl]-2-isopropyl-3,4-dimethoxyphenylacetaldehyde A mixture of 29.9 g (0.1 mole) of α-isopropyl-α-(3-chloropropyl)-3,4-dimethoxyphenylacetaldehyde and 19.5 g (0.1 mole) of N-methyl-3,4-dimethoxyphenylethylamine in 100 ml of acetonitrile was refluxed for 8 hours in the presence of 27.8 g of anhydrous potassium carbonate, while stirring thoroughly. After cooling, the reaction mixture was poured into water and extracted with twice 100 ml of ether. The ether was stripped off, after which the oily residue was purified by column chromatography (silica gel, eluent: 9:1 methylene chloride/ethanol). The isolated base was dissolved in 300 ml of hot isopropanol, and a solution of oxalic acid in isopropanol was added.

36.7 g (67%) of the hydrogen oxalate of melting point 138°–142° C. (decomposition) were isolated.

The following were obtained similarly to Example 8:

EXAMPLE 9

2-[3-[(3-Methoxyphenylethyl)-methylamino]-propyl]-2-isopropyl-3,4,5-trimethoxyphenylacetaldehyde hydrogen oxalate: m.p. 118°–120° C.

EXAMPLE 10

2-[3-[3,4-Dimethoxyphenylethyl)-methylamino]-propyl]-2-isopropyl-3,4,5-trimethoxyphenylacetaldehyde hydrogen oxalate: mp. 143°–145° C.

EXAMPLE 11

2-[3-[(3,5-Dimethoxyphenylethyl)-methylamino]-propyl]-2-isopropyl-3,5-dimethoxyphenylacetaldehyde hydrogen oxalate: mp. 97°–100° C.

EXAMPLE 12

2-[3-[(3,5-Diethoxyphenylethyl)-methylamino]-propyl]1-2-isopropyl-3,5-diethoxyphenylacetaldehyde hydrogen oxalate: mp. 115°–117° C.

The following can be obtained similarly to Examples 1 and 2:

EXAMPLE 13

2-[3-[(Phenylethyl)-methylamino]-propyl]-2-isopropyl-3,4-dichlorophenylacetaldehyde.

EXAMPLE 14

2-[3-[(3,4-Dimethoxyphenylethyl)-methylamino]-propyl]-2-isopropyl-4-nitrophenylacetaldehyde.

EXAMPLE 15

2-[3-[(3-Nitrophenylethyl)-methylamino]-propyl]-2-isopropyl-3,4,5-trimethoxyphenylacetaldehyde.

EXAMPLE 16

2-[3-[(3,4-Dimethylphenylethyl)-methylamino]-propyl]-2-isopropyl-3,5-dimethoxyphenylacetaldehyde.

EXAMPLE 17

2-[3-[(3,4-Dichlorophenylethyl)-methylamino]-propyl]-2-isopropyl-3,5-dimethoxyphenylacetaldehyde.

EXAMPLE 18

2-[3-[(4-Fluorophenylethyl)-methylamino]-propyl]-2-isopropyl-3,5-dimethoxyphenylacetaldehyde.

EXAMPLE 19

2-[3-[(3,5-Dimethoxyphenylethyl)-methylamino]-propyl]-2-isopropyl-3,4-dichlorophenylacetaldehyde.

EXAMPLE 20

2-[3-[(3,5-Diethoxyphenylethyl)-methylamino]-propyl]-2-isopropyl-3,5-dimethoxyphenylacetaldehyde.

EXAMPLE 21

2-[3-[(4-Chlorophenylethyl)-methylamino]-propyl]-2-isopropyl-3,5-dimethoxyphenylacetaldehyde.

EXAMPLE 22

2-[3-[(3-Trifluoromethylphenylethyl)-methylamino]-propyl]-isopropyl-3,5-dimethoxyphenylacetaldehyde.

EXAMPLE 23

2-[3-[3,4-Dimethoxyphenylethyl)-methylamino]-propyl]-2-isopropyl-3-trifluoromethylphenylacetaldehyde.

EXAMPLE 24

2-[3-[(3,5-Diethoxyphenylethyl)-methylamino]-propyl]-2-isopropylphenylacetaldehyde.

EXAMPLE 25

2-[3-[(3,4-Diethoxyphenylethyl)-methylamino]-propyl]-2-isopropyl-3,4,5-trimethoxyphenylacetaldehyde.

EXAMPLE 26

2-[3-[(3,4-Dimethoxyphenylethyl)-methylamino]-propyl]-2-isopropyl-4-butylphenylacetaldehyde.

EXAMPLE 27

2-[3-[(3-t-Butoxyphenylethyl)-methylamino]-propyl]-2-isopropyl-3-t-butoxyphenylacetaldehyde.

EXAMPLE 28

2-[3-[(3,3-Methylenedioxyphenylethyl)-methylamino]-propyl]-2-isopropyl-3,5-dimethoxyphenylacetaldehyde.

EXAMPLE 29

2-[3-[(3,4-Dimethoxyphenylethyl)-methylamino-propyl]-2-n-octyl-3,4,5-trimethoxyphenylacetaldehyde.

EXAMPLE 30

2-[3-[(3-Methoxyphenylethyl)-methylamino]-propyl]-2-isopropyl-1,2,3,4-tetrahydronaphthalene-6-acetaldehyde.

EXAMPLE 31

2-[3-[(Phenylethyl)-methylamino]-propyl]-2-isopropylindanyl-5-acetaldehyde.

EXAMPLE 32

2-[3-[(1,4-Benzodioxanyl-6-ethyl)-methylamino]-propyl]-2-isopropyl-3,4,5-trimethoxyphenylacetalde.

EXAMPLE 33

2-[3-[(3,5-Dimethoxyphenylethyl)-methylamino]-propyl]-2-isopropyl-3,4-ethyleneioxyphenylacetaldehyde.

EXAMPLE 34

2-[3-[(1,3-Benzodioxanyl-6-ethyl)-methylamino]-propyl]-2-isopropyl-3,4,5-trimethoxyphenylacetaldehyde.

EXAMPLE 35

2-[31-[(Phenylpropyl)-methylamino]-propyl]-2-isopropyl-3,4,5-trimethoxyphenylacetaldehyde.

EXAMPLE 36

2-[3-[(Phenylethyl)-methylamino]-propyl]-2-cyclohexylphenylacetaldehyde.

EXAMPLE 37

2-[3-[(3-Methoxyphenylethyl)-methylamino]-propyl]-2-isopropyl-3,4,5-trimethoxyphenylacetaldehyde.

EXAMPLE 38

2-[4-[(3-Methoxyphenylethyl)-methylamino]-butyl]-2-isopropylphenylacetaldehyde.

EXAMPLE A

Tablets having the following composition are pressed in a conventional manner on a tablet press:
40 mg of the substance of Example 1
120 mg of corn starch
13.5 mg of gelatine
45 mg of lactose
2.25 mg of Aerosil ® (chemically pure silica consisting of submicroscopic particles)
6.75 mg of potato starch (as a 6% strength paste)

EXAMPLE B

Coated tablets having the following composition are prepared in a conventional manner:
20 mg of the substance of Example 1
60 mg of core material
60 mg of sugar-coating material The core material consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consists of 5 parts of sucrose, 2 parts of corn starch, 2 parts of calcium carbonate and 1 part of talc. The coated tablets prepared in this manner are then provided with a coating which is resistant to gastric juice.

EXAMPLE C 10 g of the substance of Example 1 are dissolved in 5,000 ml of water with the addition of NaCl, and the solution is brought to pH 6.0 with 0.1N NaOH so that a blood-isotonic solution is formed. This solution is introduced into ampoules in an amount of 5 ml per ampoule, and sterilization is then carried out.

We claim:

1. A phenylacetaldehyde substituted by basic groups, of the formula I

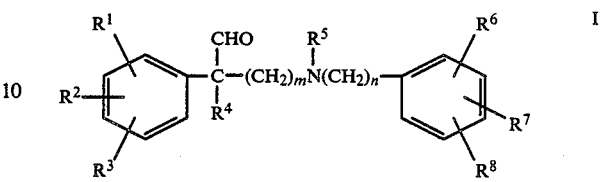

where $R^1$, $R^2$, $R^3$, $R^6$, $R^7$ and $R^8$ are identical or different and are each hydrogen, halogen, trifluoromethyl, $C_1$–$C_4$-alkyl, nitro or $C_1$–$C_4$-alkoxy, and two radicals in adjacent positions may furthermore together form methylenedioxy, ethylenedioxy, 1,3-dioxatetramethylene, propylene or butylene, $R_4$ is a saturated or unsaturated $C_1$–$C_{12}$-alkyl group, a cycloalkyl group or an aryl group, $R^5$ is $C_1$–$C_4$-alkyl and m and n are identical or different and are each 2, 3 or 4, and its salts with physiologically tolerated acids.

2. (RS)-2-[3-[(Phenylethyl)-methylamino]-propyl]-2-isopropylphenylacetaldehyde and its enantiomers.

3. (RS)-2-[3-[(3-Methoxyphenylethyl)-methylamino]-propyl]-2-isopropyl-3,4-dimethoxy henylacetaldehyde and its enantiomers.

4. (RS)-2-[3-[(3-Methoxyphenylethyl)-methylamino]-propyl]-2-isopropyl-3,4,5-trimethoxyphenylacetaldehyde and its enantiomers.

5. (RS)-2-[3-[(3,5-Dimethoxyphenylethyl)-methylamino]1-propyl]-2-isopropyl-3,5-dimethoxyphenylacetaldehyde and its enantiomers.

6. (RS)-2-[3-[(3-Ethoxyphenylethyl)-methylamino]-propyl]-2-isopropyl-3-ethoxyphenylacetaldehyde and its enantiomers.

7. (RS)-2-[3-[(3,5-Diethoxyphenylethyl)-methylamino]propyl]-2-isopropyl-3,5-diethoxyphenylacetaldehyde and its enantiomers.

8. A method of treating circulatory disorders including cardiac diseases, high blood pressure, and disturbances of blood flow which comprises administering to a patient suffering from such a disorder an effective amount of a compound of the formula I as described in claim 1 or its salts with physiologically tolerated acid.

9. A method of treating gastric and duodenal ulcers which comprises administering to a patient suffering from said ulcers an effective amount of a compound of the formula I as described in claim 1 or its salts with physiologically tolerated acids.

* * * * *